US010086153B2

(12) United States Patent
Korneff

(10) Patent No.: US 10,086,153 B2
(45) Date of Patent: Oct. 2, 2018

(54) BREATH ACTUATED NEBULIZER HAVING A PRESSURIZED GAS DIVERTER WITH A DIVERTER ORIFICE

(71) Applicant: CareFusion 207, Inc., San Diego, CA (US)

(72) Inventor: Neil Korneff, Diamond Bar, CA (US)

(73) Assignee: CareFusion 207, Inc., San Diego, CA (US)

(*) Notice: Subject to any disclaimer, the term of this patent is extended or adjusted under 35 U.S.C. 154(b) by 634 days.

(21) Appl. No.: 14/702,604

(22) Filed: May 1, 2015

(65) Prior Publication Data

US 2015/0231341 A1 Aug. 20, 2015

Related U.S. Application Data

(63) Continuation of application No. 13/539,204, filed on Jun. 29, 2012, now Pat. No. 9,022,023.

(51) Int. Cl.

*A61M 11/00* (2006.01)
*A61M 11/02* (2006.01)
*A61M 15/00* (2006.01)

(52) U.S. Cl.

CPC ........... *A61M 11/02* (2013.01); *A61M 11/007* (2014.02); *A61M 15/0095* (2014.02); *A61M 2205/583* (2013.01)

(58) Field of Classification Search

CPC .............. A61M 11/06; A61M 15/0093; A61M 2205/583; A61M 11/02; A61M 11/007; A61M 15/0095

See application file for complete search history.

(56) References Cited

U.S. PATENT DOCUMENTS

| | | | | |
|---|---|---|---|---|
| 5,533,497 | A * | 7/1996 | Ryder | B05B 7/0012 128/200.21 |
| 5,687,912 | A | 11/1997 | Denyer | |
| 5,823,179 | A | 10/1998 | Grychowski et al. | |
| 6,044,841 | A | 4/2000 | Verdun et al. | |
| 6,129,080 | A * | 10/2000 | Pitcher | A61M 11/06 128/200.14 |
| 6,450,163 | B1 | 9/2002 | Blacker et al. | |
| 6,612,303 | B1 | 9/2003 | Grychowski et al. | |
| 6,644,304 | B2 | 11/2003 | Grychowski et al. | |
| 6,748,945 | B2 | 6/2004 | Grychowski et al. | |
| 6,804,656 | B1 | 10/2004 | Rosenfeld et al. | |
| 6,929,003 | B2 | 8/2005 | Blacker et al. | |
| 6,994,083 | B2 | 2/2006 | Foley et al. | |
| 7,080,643 | B2 | 7/2006 | Grychowski et al. | |
| 7,131,439 | B2 | 11/2006 | Blacker et al. | |
| 7,207,945 | B2 | 4/2007 | Bardy | |
| 7,270,123 | B2 | 9/2007 | Grychowski et al. | |
| RE40,591 | E | 12/2008 | Denyer | |
| 7,559,322 | B2 | 7/2009 | Foley et al. | |
| 7,568,480 | B2 | 8/2009 | Foley et al. | |
| 7,634,995 | B2 | 12/2009 | Grychowski et al. | |
| 7,721,729 | B2 | 5/2010 | Denyer | |
| 7,841,335 | B2 | 11/2010 | Harrington et al. | |

(Continued)

*Primary Examiner* — Steven Douglas

(74) *Attorney, Agent, or Firm* — McDermott Will & Emery LLP

(57) ABSTRACT

A nebulizer is provided that includes an internal medication chamber and a pressurized gas diverter. The internal medication chamber is configured for holding a medication. The pressurized gas diverter includes a diverter orifice.

20 Claims, 15 Drawing Sheets

Section I-I

(56) References Cited

U.S. PATENT DOCUMENTS

| | | | |
|---|---|---|---|
| 7,841,336 | B2 | 11/2010 | Rivera et al. |
| 7,905,228 | B2 | 3/2011 | Blacker et al. |
| 7,954,487 | B2 | 6/2011 | Grychowski et al. |
| 7,959,574 | B2 | 6/2011 | Bardy |
| RE42,911 | E | 11/2011 | Denyer |
| 8,056,557 | B2 | 11/2011 | Lieberman et al. |
| 8,061,352 | B2 | 11/2011 | Grychowski et al. |
| 9,757,528 | B2 * | 9/2017 | Rubin .................... A61M 11/02 |
| 2003/0079743 | A1 | 5/2003 | Genova et al. |
| 2007/0023036 | A1 | 2/2007 | Grychowski et al. |
| 2007/0107719 | A1 | 5/2007 | Blacker et al. |
| 2007/0186927 | A1 | 8/2007 | Djupesland et al. |
| 2007/0204864 | A1 | 9/2007 | Grychowski et al. |
| 2008/0083407 | A1 | 4/2008 | Grychowski et al. |
| 2009/0272820 | A1 | 11/2009 | Foley et al. |
| 2011/0168169 | A1 | 7/2011 | Blacker et al. |
| 2012/0000461 | A1 | 1/2012 | Grychowski et al. |
| 2012/0138054 | A1 | 6/2012 | Hearn et al. |

* cited by examiner

Section II-II

Section I-I

Section I-I

1400 ⤴

1410 — Begin

1420 — Receive pressurized gas into a pressurized gas diverter at a diverter orifice from a gas outlet orifice associated with a nozzle assembly 1440 — When the opening is at least substantially sealed, create medical aerosol 1450 — When the opening is not at least substantially sealed, reduce creation of medical aerosol 1460 — End

BREATH ACTUATED NEBULIZER HAVING A PRESSURIZED GAS DIVERTER WITH A DIVERTER ORIFICE

CROSS-REFERENCE TO RELATED APPLICATION

This application is a continuation application of U.S. patent application Ser. No. 13/539,204, U.S. Pat. No. 9,022,023, entitled "BREATH ACTUATED NEBULIZER HAVING A PRESSURIZED GAS DIVERTER WITH A DIVERTER ORIFICE," filed Jun. 29, 2012, the entire contents of which are incorporated by reference herein.

FIELD OF THE INVENTION

The present technology relates generally to nebulizers. More particularly, the present technology relates to a breath actuated nebulizer having a pressurized gas diverter.

BACKGROUND

Nebulizers can be used for treating living beings that are capable of spontaneous breathing or living beings that are using controlled ventilation mechanisms, among other things. Nebulizers can be used to create a fine spray of medication with small particles of medication suspended in gas (also referred to herein as "medical aerosol") that can be inhaled by the living being. Medication in the form of liquid or a solid, among other things, can be placed inside of the nebulizer. The nebulizer can be used to mix gas with the medication inside of the nebulizer to create the medical aerosol that is delivered to the living being through a mouth piece associated with the nebulizer.

BRIEF SUMMARY OF THE INVENTION

According to one embodiment, a breath actuated nebulizer is provided that creates medical aerosol in response to a living being breathing and prevents creation of medical aerosol in response to a lack of breathing. According to one embodiment, a breath actuated nebulizer is provided that creates a medical amount of medical aerosol for treating the living being in response to a living being breathing in through the nebulizer and reduces creation of medical aerosol in response to a lack of breathing in through the nebulizer or exhalation through the nebulizer or inhalation that falls below a specified level.

DETAILED DESCRIPTION

Nebulizers can be used for creating medical aerosol for treating living beings. A nebulizer that continuously creates medical aerosol wastes medication because medical aerosol escapes into the air without the living being breathing it. Further, other living beings that are in the environment may be subjected to the medical aerosol that escapes into the air. Examples of living beings are people and animals.

Therefore, according to one embodiment, a breath actuated nebulizer is provided that creates medical aerosol in response to a living being breathing and prevents creation of medical aerosol in response to a lack of breathing. According to one embodiment, a breath actuated nebulizer is provided that creates a medical amount of medical aerosol for treating the living being in response to a living being breathing in through the nebulizer and reduces creation of medical aerosol in response to a lack of breathing in through the nebulizer or exhalation through the nebulizer or inhalation that falls below a specified level.

The term "medical amount" is defined as an amount of medical aerosol that would be used for treating a living being using that type of medical aerosol. The term "reduced" is defined as "reduced" in comparison to the amount of medical aerosol is created when the living being is breathing in through the nebulizer. According to various embodiments, the amount of medical aerosol created when the living being is not breathing in through the nebulizer is less than the amount of medical aerosol created by legacy breath actuated nebulizers that continuously create medical aerosol regardless of whether a living being is breathing in through the nebulizer or not. According to one embodiment, an insignificant amount of medical aerosol may be created when there is a lack of inhalation through the nebulizer. An insignificant amount of medical aerosol is defined as an amount that does not treat or affect a living being.

Figure 1:
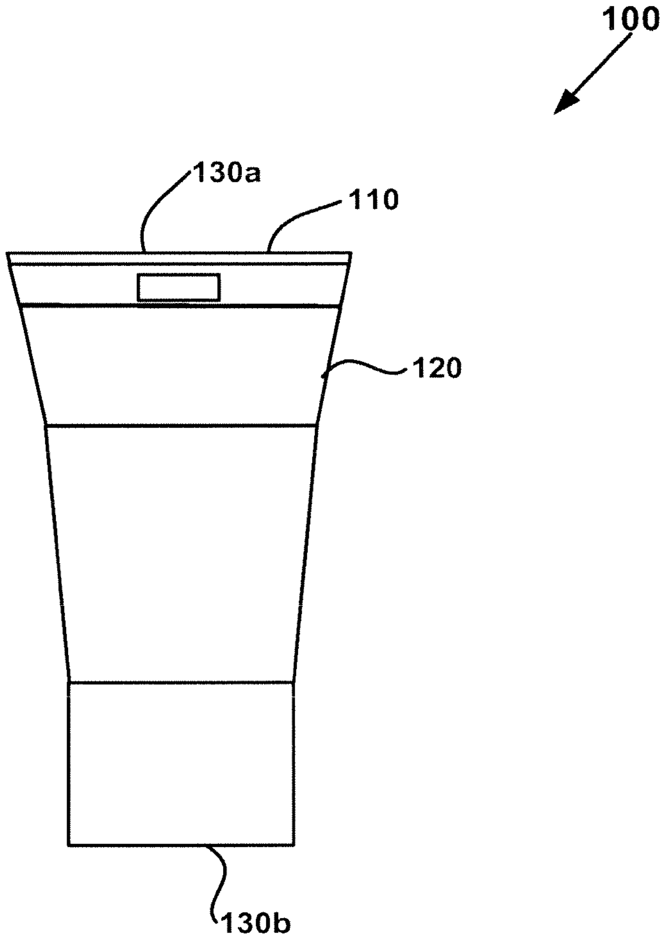
FIG. 1 depicts a back view of the outside of a nebulizer, according to one embodiment.

FIG. 1 depicts a back view of the outside of a nebulizer 100, according to one embodiment. As depicted in FIG. 1, the nebulizer 100 has a housing 120 on the outside. The nebulizer has a top 130*a* and a bottom 130*b*. A cover 110 can be located on the top 130*a* of the nebulizer 100. A nebulizer 100 can be used for treating living beings that are capable of spontaneous breathing (inhalation and exhalation) or living beings that are using controlled ventilation mechanisms, among other things.

Figure 2:
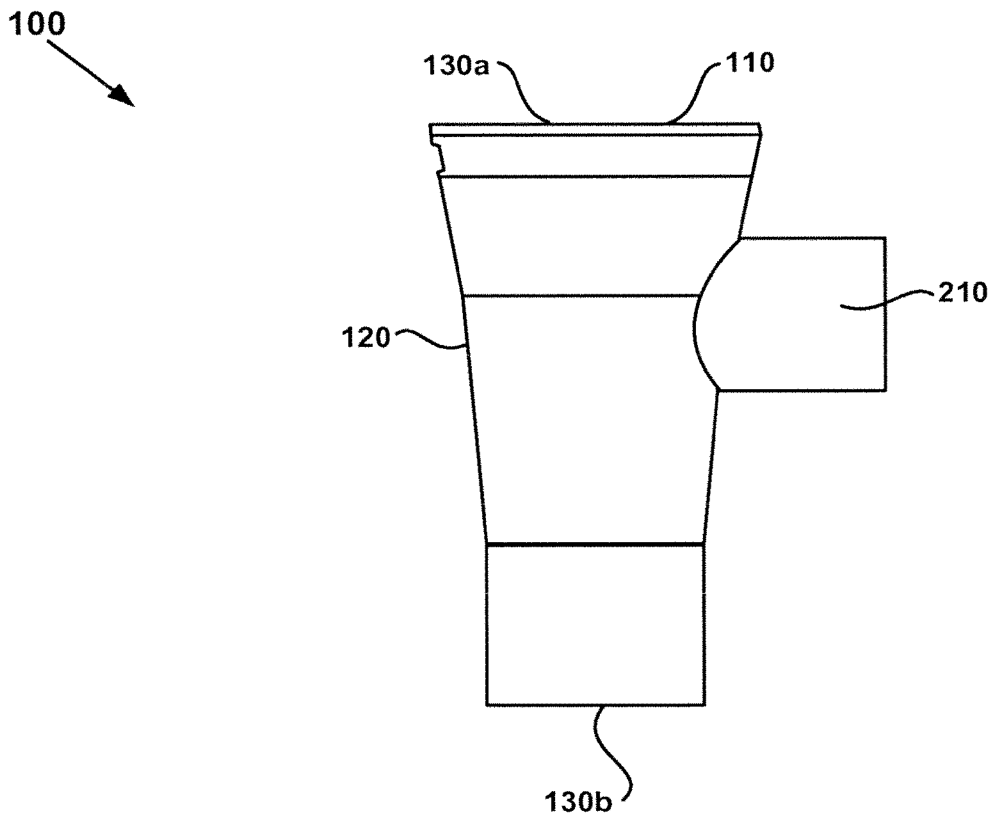
FIG. 2 depicts a side view of the outside of a nebulizer, according to one embodiment.
Figure 3:
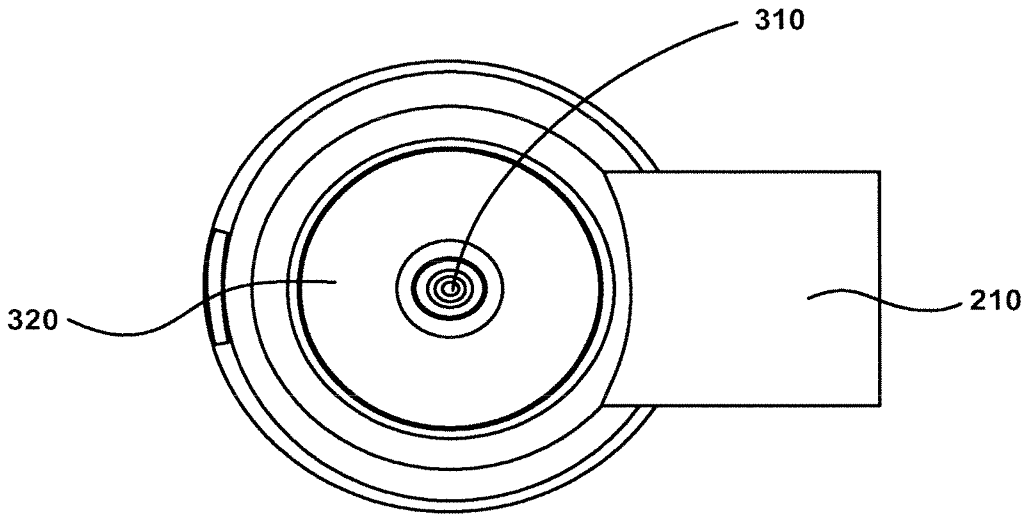
FIG. 3 depicts a bottom view of a nebulizer, according to one embodiment.

FIG. 2 depicts a side view of the outside of a nebulizer 100, according to one embodiment. The chamber air outlet 210 can be seen from the side view. FIG. 3 depicts a bottom view of a nebulizer 100, according to one embodiment. The bottom 130*b* of the pressurized gas fitting 310 and the outer chamber 320 can be seen in FIG. 3.

With reference to FIGS. 2 and 3, pressurized gas can be provided from a supply to a pressurized gas fitting 310 (FIG. 3) that is located toward the bottom 130*b* of the nebulizer 100. A living being can inhale medical aerosol by placing their mouth on the chamber air outlet 210. The pressurized gas travels through the nebulizer 100 and mixes with the medication, in the form of liquid or a solid, among other things, to provide medical aerosol that is then supplied to the living being through the chamber air outlet 210. According to one embodiment, medical aerosol is a fine spray of medication with small particles of medication suspended in gas.

Figure 4:
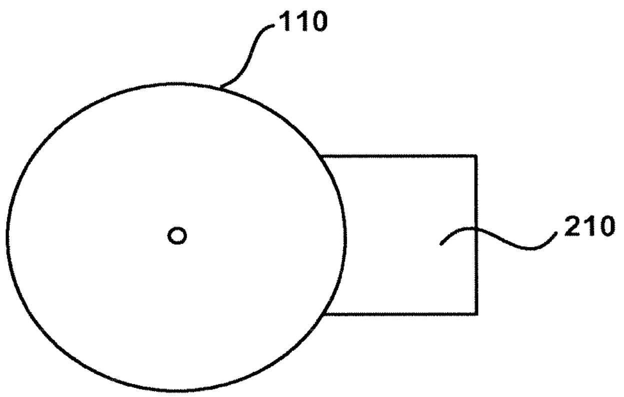
FIG. 4 depicts a top view of a nebulizer, according to one embodiment.

FIG. 4 depicts a cover 110 of a nebulizer 100, according to one embodiment. The cover 110 is located at the top 130*a* of the nebulizer 100.

Figure 5:
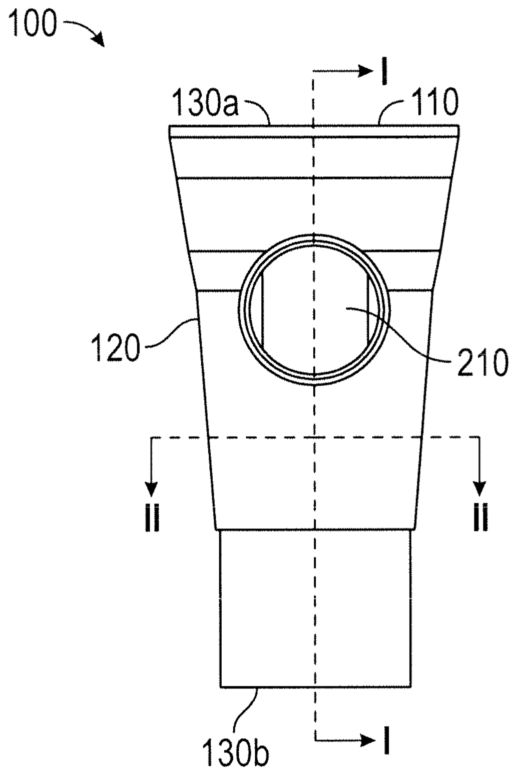
FIG. 5 depicts a front view of a nebulizer, according to one embodiment.

FIG. 5 depicts a front view of a nebulizer 100, according to one embodiment. The outlet 210 is located at the front of the nebulizer 100. FIG. 5 depicts cross sections I-I and II-II. Cross section II-II corresponds to FIGS. 6A and 6B. Cross Section I-I corresponds to FIGS. 7, 9, and 10-12.

Figure 6A:
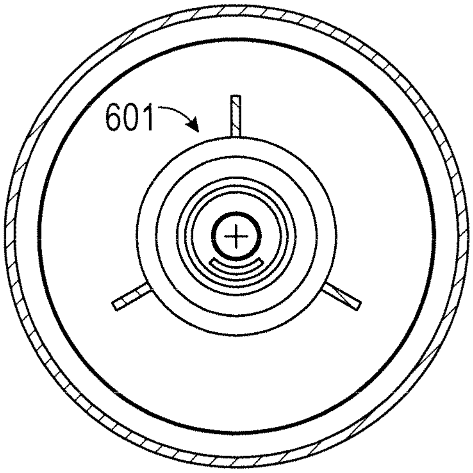
FIG. 6A depicts a cross section of the nebulizer in FIG. 5 at cross section II-II, according to one embodiment.
Figure 6B:
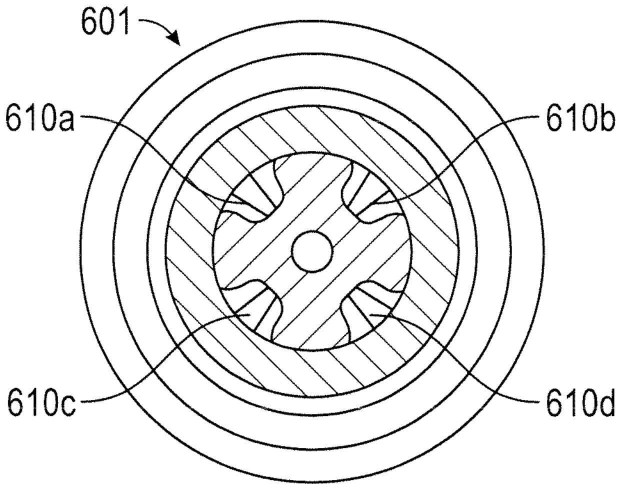
FIG. 6B depicts a zoomed in view of liquid outlet orifices, according to one embodiment.

FIG. 6A depicts a cross section of the nebulizer in FIG. 5 at cross section II-II, according to one embodiment. Inside of the cross section II-II is a nozzle top 601. FIG. 6B depicts the nozzle top 601 with liquid outlet orifices 610*a-d*, according to one embodiment. Medication can be placed in an internal medication chamber of the nebulizer. When the nebulizer's diverter is actuated, as will become more evident, pressurized gas can shear across the surface of the liquid outlet orifices 610*a-d* and move into the internal medication chamber and mix with medication to create medical aerosol. "Shearing across" shall be defined, according to one embodiment, as the pressurized gas moving across the surface.

Although various embodiments have been described as sealing the top opening of the diverter as a part of creating medical aerosol, various embodiments are well suited for substantially sealing the top opening as a part of creating medical aerosol. For example, as long as the diverter's top opening is sufficiently sealed so that a sufficient amount of gas shears across the surface of the liquid outlet orifices 610 (FIG. 6B), medical aerosol can be created, as will become more evident.

Figure 7:
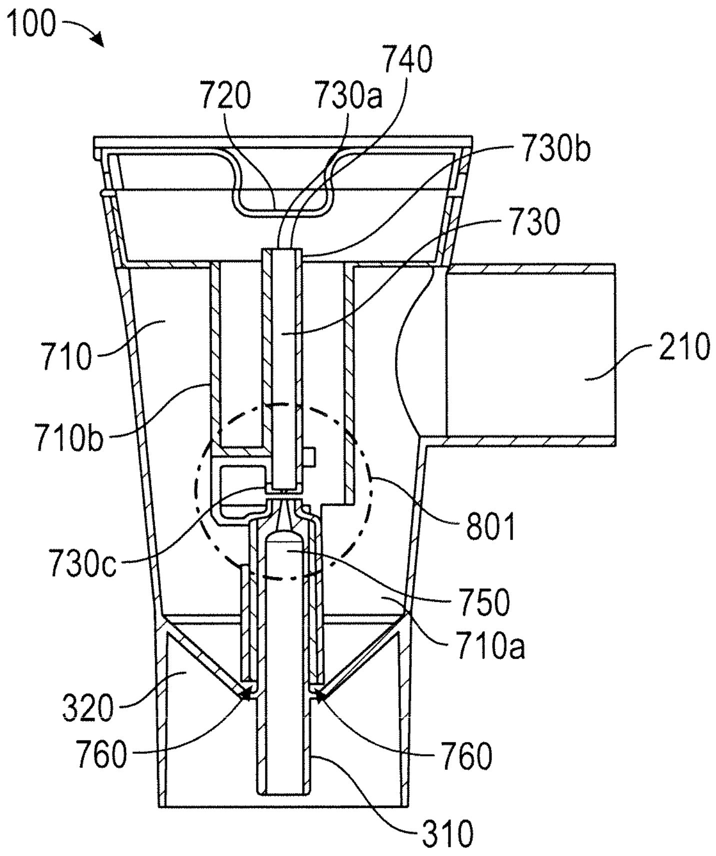
FIG. 7 depicts a cross section of the nebulizer in FIG. 5 at cross section I-I while the diverter is deactuated, according to one embodiment.

FIG. 7 depicts a cross section I-I of the nebulizer 100 in FIG. 5 while the diverter 730 is deactuated, according to one embodiment. The diverter 730 is deactuated during periods of non-inhalation, according to one embodiment.

The nebulizer 100 includes a diverter-actuator-deactuator 720, an internal medication chamber 710, a lower portion 710*a* of the internal medication chamber 710, walls 710*b* of the internal medication chamber 710, liquid reservoir openings 760, a chamber air outlet, a pressurized gas diverter 730, the diverter top 730*b*, the diverter 730, a nozzle assembly 750, a pressurized gas fitting 310, and a nozzle area 801.

The pressurized gas diverter 730 includes a wall that encompasses an inner chamber, and a diverter orifice located toward the bottom 730*c* of the diverter 730 and an opening 730*a* located at the top 730*b*.

The diverter-actuator-deactuator 720 can be located toward the top 730*b* of the nebulizer 100. The diverter-actuator-deactuator 720 can be attached to the top 730*b* of the nebulizer 100, for example, by attaching the diverter-actuator-deactuator 720 to the lower surface of the cover 110. According to one embodiment, the diverter-actuator-deactuator 720 has a bowl shape and is made of a flexible material, such as silicon. The diverter-actuator-deactuator 720 can be manufactured to provide enough force to adequately seal the opening 730*a*. The diverter-actuator-deactuator 720 can stretch to seal and then return to its original shape or approximately to its original shape to unseal, as will become more evident.

Although various embodiments are described in the context of a bowl shaped diverter-actuator-deactuator 720 made of flexible material, embodiments are well suited for other types of diverter-actuator-deactuators. For example, a piston-like diverter-actuator-deactuator could be used. Any type of diverter-actuator-deactuator 720 that can be used for sufficiently sealing the opening 730*a* at the top 730*b* of the diverter 730 in response to a living being's inward breath (inhalation) and sufficiently unsealing the opening 730*a* in response to a lack of inward breath can be used. The phrase "lack of breath" shall be used to refer to when inhalation through nebulizer 100 has not started yet and to when inhalation through nebulizer 100 stops after it has started.

The diverter-actuator-deactuator 720, according to one embodiment, is aligned with the opening 730*a* at the top 730*b* of the diverter 730 so that the diverter-actuator-deactuator 720 can seal and unseal the opening 730*a* as described herein.

The diverter 730 includes an inner chamber, a wall, an opening 730*a* at the top 730*b* and a diverter orifice at the diverter bottom 730*c*. The diverter 730, according to one embodiment, has a length that ranges from 30% to 50% of the length of the nebulizer 100. According to one embodiment, the diverter 730 is approximately 40% the length of the nebulizer 100. From a side view, the diverter 730 can be located approximate in the middle portion of the nebulizer 100. From a top view, the diverter 730 can be located approximately in the center of the nebulizer 100.

The nozzle assembly 750 includes an inner chamber and walls that form the inner chamber. The nozzle assembly 750 also includes a gas outlet orifice at the top of the nozzle assembly 750 and a pressurized gas fitting toward the bottom 130*b* of the nebulizer 100.

The nozzle assembly 750, according to one embodiment, has a length that ranges from 30% to 50% of the length of the nebulizer 100. According to one embodiment, the nozzle assembly 750 is approximately 40% the length of the nebulizer 100. According to one embodiment, the diverter 730 and the nozzle assembly 750 are approximately equal in length. According to one embodiment, the inner chambers of the respective diverter 730 and nozzle assembly 750 are approximately equal in diameter. From the top view, the nozzle assembly 750 can be located approximately at the center of the nebulizer 100. The diverter orifice at the bottom 730*c* of the diverter 730 is aligned with the liquid outlet orifice 610 (FIG. 6B) at the top of the nozzle assembly 750.

The liquid outlet orifices 610 (FIG. 6B) are located toward the top of the nozzle assembly 750, according to one embodiment.

The internal medication chamber 710, according to one embodiment, is located approximately in the middle of the nebulizer 100 when viewed from the side. The internal medication chamber 710, according to one embodiment, surrounds most of the diverter 730 and at least an upper portion of the nozzle assembly 750. According to one embodiment, a small portion of the diverter 730 extends above the internal medication chamber 710 to enable the diverter-actuator-deactuator 720 to properly seal the diverter 730's top opening 730*a*.

The chamber air outlet 210 is located on the side of the nebulizer 100 and is connected with the internal medication chamber 710 so that medical aerosol can travel from the internal medication chamber 710 into and out of the chamber air outlet 210.

Medication can be placed in the lower portion 710*a* of the internal medication chamber 710. A supply of pressurized gas can be coupled to with the pressurized gas fitting 310. Medical aerosol can be supplied to a living being through the chamber air outlet 210.

Figure 9:
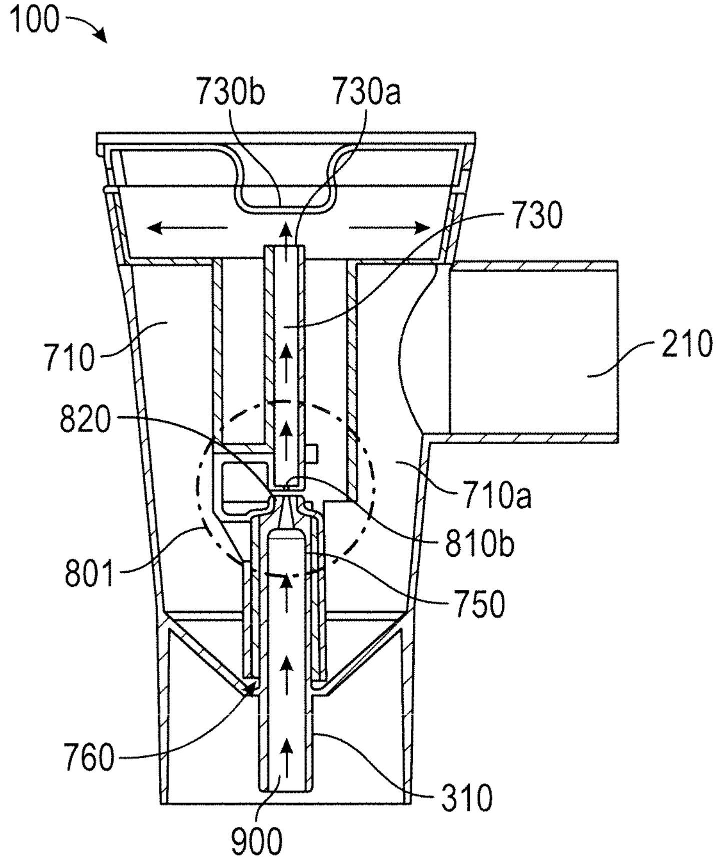
FIG. 9 depicts a flow of pressurized gas when the diverter is deactuated, according to one embodiment.
Figure 10:
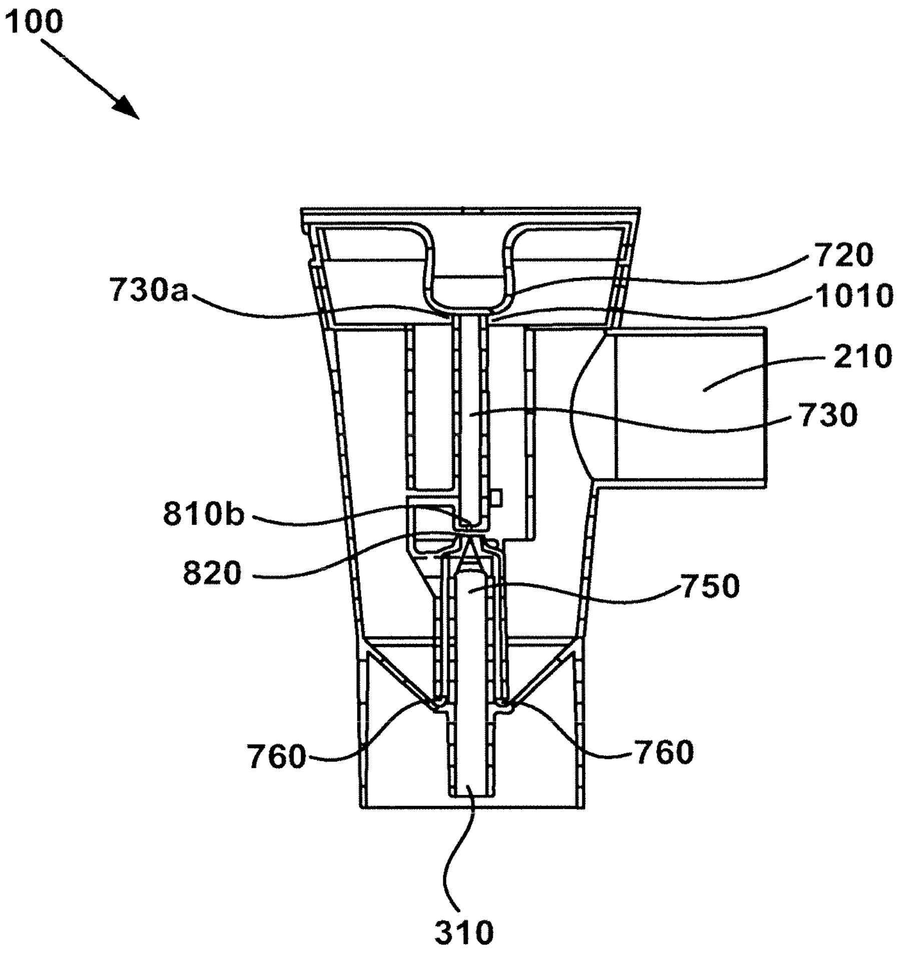
FIG. 10 depicts a cross section of the nebulizer in FIG. 5 at cross section I-I while the diverter is actuated, according to one embodiment.
Figure 11:
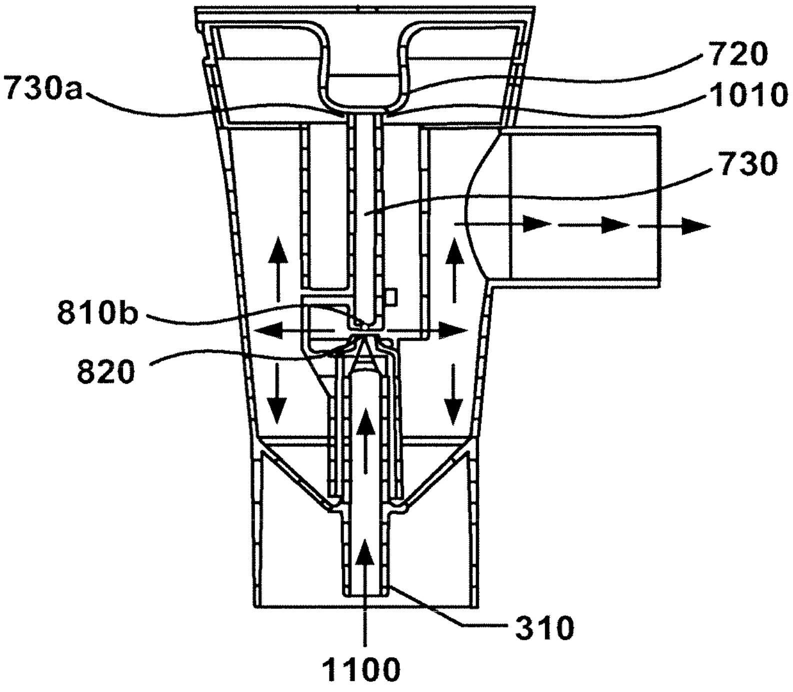
FIG. 11 depicts a flow of pressurized gas when the diverter is actuated, according to one embodiment.
Figure 12:
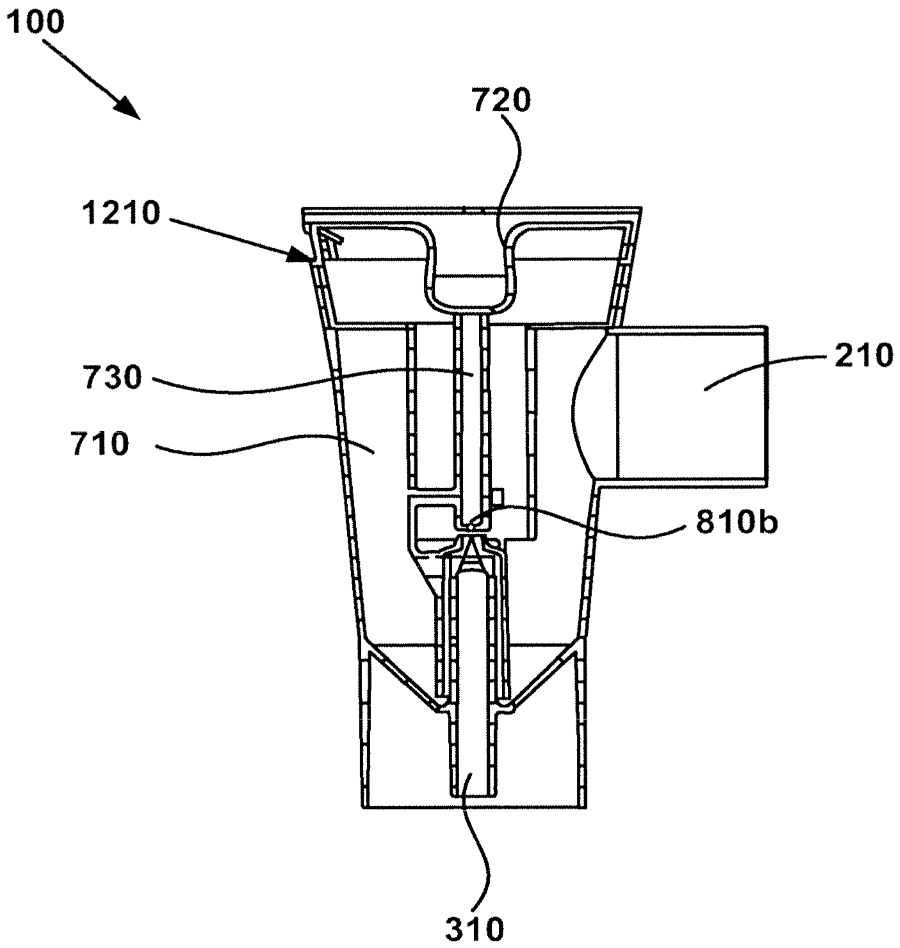
FIG. 12 depicts a cross section of the nebulizer in FIG. 5 at cross section I-I while the diverter is actuated, according to another embodiment.

As will become more evident, the diverter-actuator-deactuator 720 seals the top opening 730*a* of the diverter 730, as depicted in FIGS. 7 and 9, in response to a living being inhaling through chamber air outlet 210 and does not seal the top opening 730*a* of the diverter 730 in response to exhalation or a lack of any breathing (inhalation or exhalation) through chamber air outlet 210. When the top opening 730*a* is not sealed, as depicted in FIGS. 10-12, pressurized gas is allowed to pass through gas diverter orifice 810*b*, through pressurized gas diverter 730, and out of top opening 730*b* thus, reducing or preventing the creation of medical aerosol. Therefore, the lack of a seal at the top opening 730*a* is also referred to as "deactuates gas diversion" or "medical aerosol creation mode". When the top opening 730*a* is sealed, gas cannot pass through gas diverter orifice 810*b* and is instead diverted such that it shears across the surface of the liquid outlet orifices 610, thus, enabling the creation of medical aerosol. Therefore, the sealing of the top opening 730*a* is also referred to as "actuates gas diversion" or "gas diversion mode."

It should be appreciated that such gas diversion to create medical aerosol does not rely upon movement of gas diverter orifice 810*b*, pressurized gas diverter 730, or any of liquid outlet orifices 610. It should also be appreciated that that the gap between gas outlet orifice 820 and gas diverter orifice 810*b* is the same when medical aerosol is being created and when medical aerosol is not being created. Similarly, the gap between gas diverter orifice 810*b* and each of liquid outlet orifices 610 is the same when medical aerosol is being created and when medical aerosol is not being created. Additionally, it should be noted that medical aerosol creation takes place without the use of any sort of movable shield proximate to gas diverter orifice 810*b*, liquid outlet orifices 610, nozzle assembly 750, or gas outlet orifice 820.

Figure 8:
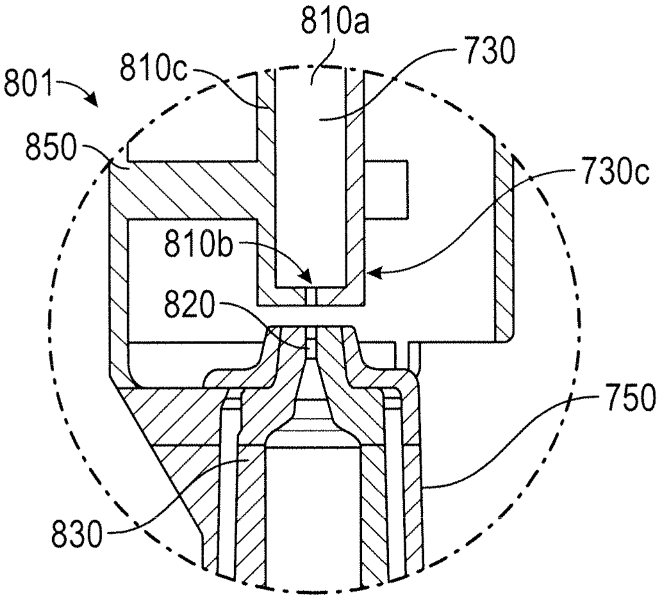
FIG. 8 depicts an exploded view of a diverter orifice, according to one embodiment.

FIG. 8 depicts an exploded view of the nozzle area 801, according to one embodiment. FIG. 8 depicts the upper portion of the nozzle assembly 750 and the lower portion of the pressurized gas diverter 730. The pressurized gas diverter 730 includes a wall 810*c* that encompasses an inner chamber 810*a*, a diverter orifice 810*b* located toward the bottom 730*c* of the diverter 730 and an opening 730*a* (FIG. 7) located toward the top 730*b* (FIG. 7) of the diverter 730. FIG. 8 also depicts a support beam 850 for attaching the diverter 730 to a wall 710*b* (FIG. 7) of the internal medication chamber 710 (FIG. 7).

FIG. 9 depicts a flow 900 of pressurized gas when the diverter 730 is deactuated, according to one embodiment. The diverter 730 is deactuated during periods of non-inhalation due to the opening 730*a* at the top 730*b* of the diverter 730 not being sealed, according to one embodiment. For example, pressurized gas can enter the nozzle assembly 750 through the pressurized gas fitting 310. The pressurized gas can travel up the inner chamber of the nozzle assembly 750 and out the gas outlet orifice 820 located at the top of the nozzle assembly 750. A significant amount of the gas can then move into the pressurized gas diverter 730 through the diverter orifice 810*b* and out the opening 730*a* located at the top 730*b* of the diverter 730. A first portion of the gas that entered the diverter 730 can be vented out of the nebulizer 100 through various openings in the nebulizer 100 without exiting the chamber air outlet 210. A second portion of the gas that entered the diverter 730 may travel to the internal medication chamber 710, however, according to various embodiments, the second portion of gas does not come into close enough proximity of the liquid outlet orifices 610 (FIG. 6B) to produce medical aerosol.

FIG. 10 depicts a cross section I-I of the nebulizer 100 in FIG. 5 while the diverter 730 is actuated, according to one embodiment. The diverter 730 is actuated, according to one embodiment, during periods of inhalation. As depicted in FIG. 10, the diverter-actuator-deactuator 720 has stretched to close the diverter 730's top opening 730*a*, thus, sealing the diverter 730 (also referred to herein as "diverter seal 1010").

FIG. 11 depicts a flow 1100 of pressurized gas when the diverter 730 is actuated, according to one embodiment. During the initial inhalation, the living being can overcome the flow being introduced into the nebulizer 100 through the gas outlet orifice 820. For example, if an amount of gas, such as 8 LPM of gas, is being introduced into the nebulizer 100 through the pressurized gas fitting 310, the living being could inhale more than that same amount of gas, which in this example is 8 LPM, to start producing a negative gage pressure in the internal medication chamber 710. Once the living being's breathing has produced a negative gauge pressure in the internal medication chamber 710, the diverter-actuator-deactuator 720 can move down and seal the diverter opening 730*a* creating a "diverter seal 1010." If the living being's breathing allows the negative gauge pressure to cease (e.g., through reduced inhalation or through exhalation) this seal of diverter opening 730*a* will cease as well. The diverter seal 1010 prohibits gas from exiting the diverter opening 730*a* and prevents additional gas from entering the diverter orifice 810*b* from the nozzle assembly 750's gas outlet orifice 820. Therefore, gas is forced to travel in proximity of the liquid outlet orifices 610 (FIG. 6B) enabling pressurized gas to enter the internal medication chamber 710 and mix with the medication resulting in medical aerosol. The medical aerosol can then travel from the internal medication chamber 710 to the living being through the outlet 210.

FIG. 12 depicts a cross section I-I of the nebulizer 100 in FIG. 5 while the diverter is actuated, according to another embodiment. According to one embodiment, the nebulizer 100 includes an additional air inlet valve 1210. For example, a living being's physiological peak inhalation flow can exceed the flow being delivered into the nebulizer 100 through the gas outlet orifice 820 (FIG. 8). Continuing the example, a living being may have a physiologically peak inhalation flow of 20 LPM, but in this example the nebulizer 100 is only receiving 8 LPM through the pressurized gas fitting 310. The additional air inlet valve 1210 can open up enabling ambient air to enter the nebulizer 100, thus, enhancing the aerosol performance.

Various embodiments have been illustrated with 8 LPM received from the pressurized gas fitting 310 and 20 LPM for the living being's physiological peak inhalation rate. However, these are only examples. Various embodiments are well suited to other levels.

According to one embodiment, the additional air inlet valve 1210 is constructed to maintain a predetermined negative pressure in the internal medication chamber 710 at various inhalation flow rates in order to ensure, according to one embodiment, that even if the additional air inlet valve 1210 opens, the diverter-actuator-deactuator 720 can maintain the diverter seal 1010 with respect to the opening 730*a* at the top of the diverter 730.

As can be seen, the pressure in the internal medication chamber 710 fluctuates in response to a living being's breathing through nebulizer 100, where their breathing creates more pressure at one point in time and less pressure at another point in time, their lack of breathing, the amount of pressurized gas supplied through the pressurized gas fitting 310, the response and design of the additional air inlet valve 1210, among other things. According to one embodiment, the pressure within the internal medication chamber 710 fluctuates in response to a living being's breathing through the outlet 210. Further, according to one embodiment, an amount of flow through the diverter orifice 810*b* responds to fluctuations of pressure within the internal medication chamber 710.

According to one embodiment, a diverter override mechanism is provided for overriding the pressurized gas diverter. For example, a living being may want to override the breath deactuated capabilities of the nebulizer 100 to cause a nebulizer 100 to continuously create medical aerosol regardless of whether the living being is breathing through nebulizer 100 or not.

Figure 13A:
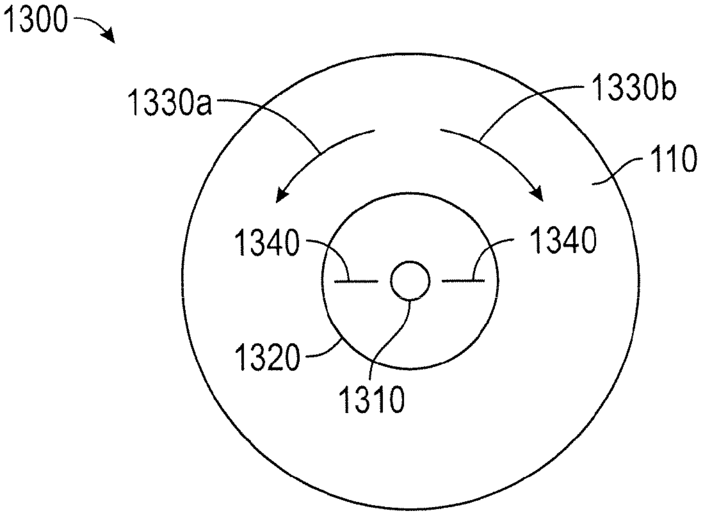
FIG. 13A depicts a top view of a diverter override mechanism, according to one embodiment.

FIG. 13A depicts a top view of a diverter override mechanism 1300, according to one embodiment. The diverter override mechanism 1300 can be located at and incorporated into the nebulizer's cover 110, among other things. The diverter override mechanism 1300 can include a button 1310, for example. Optionally, the diverter override mechanism 1300 can include a rotatable flange 1320. The rotatable flange 1320 can include tabs 1340 to make it easier for a living being to grasp. The button 1310 can be pushed to override the breath deactuated capabilities of the nebulizer causing the nebulizer to continuously create medical aerosol regardless of whether a living being is breathing into the nebulizer. If the flange 1320 is rotated in one direction 1330*a*, the button 1310 cannot be pressed to override the breath deactuated capabilities. If the flange 1320 is rotated in the other direction 1330*b*, the button 1310 can be pressed to override the breath deactuated capabilities. The directions 1330*a*, 1330*b* can be reversed. Although the diverter override mechanism 1300 is illustrated using a button 1310, various embodiments are well suited to other types of mechanisms for overriding the breath actuated capabilities besides a button 1310, such as a lever, among other things.

Figure 13B:
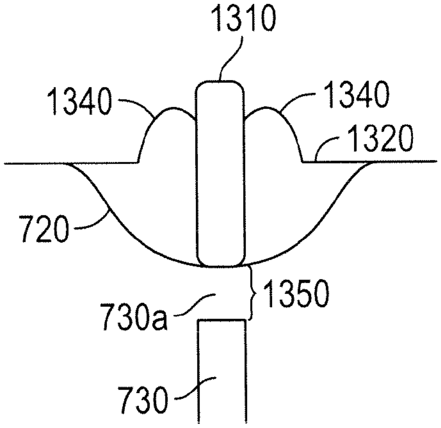
FIG. 13B depicts a cross section of the diverter override mechanism when it is not in override mode, according to one embodiment.

FIG. 13B depicts a side cross section of the diverter override mechanism 1300 when it is not in override mode, according to one embodiment. In FIG. 13B, the button 1310 is not pressed down. Therefore, there is a gap 1350 between the diverter-actuator-deactuator 720 and the diverter 730's top opening 730*a*. Thus, the breath deactuated capabilities of the nebulizer are not overridden.

Figure 13C:
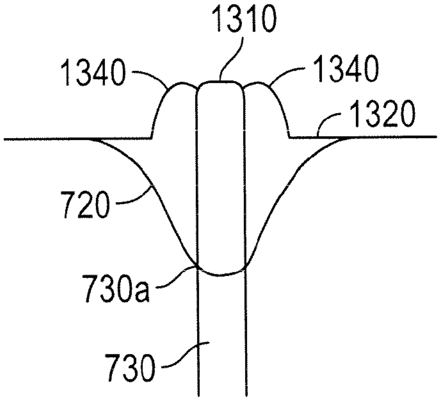
FIG. 13C depicts a cross section of the diverter override mechanism in override mode, according to one embodiment.

FIG. 13C depicts a side cross section of the diverter override mechanism 1300 in override mode, according to one embodiment. In FIG. 13C, the button 1310 is pressed down. Therefore, the button 1310 is pushing the diverter-actuator-deactuator 720 so that it seals the diverter 730's top opening 730*a*. Thus, the breath deactuated capabilities of the nebulizer are overridden. A living being pushing the button 1310 to override the breath deactuated capabilities is also referred to as "operator intervention." Therefore, according to one embodiment, an amount of flow through the diverter orifice responds to an operator intervention.

According to one embodiment, a button 1310 as depicted in FIGS. 13A-13C can be used as a visual indication of whether the nebulizer 100 is in diversion mode or not in diversion mode. For example, the button 1310 will be up when the opening 730*a* is not sealed and will be down when the opening 730*a* is sealed, thus, providing a visual indication of whether the nebulizer 100 is in diversion mode or not in diversion mode. The button 1310 is referred to herein as "a visual indicator." According to one embodiment, the button 1310 will move up and down by various amounts in response to pressure fluctuations in the internal medication chamber. Therefore, according to one embodiment, pressure fluctuations within the internal medication chamber can be visually indicated through the mechanical movement of a visual indicator.

Figure 14:
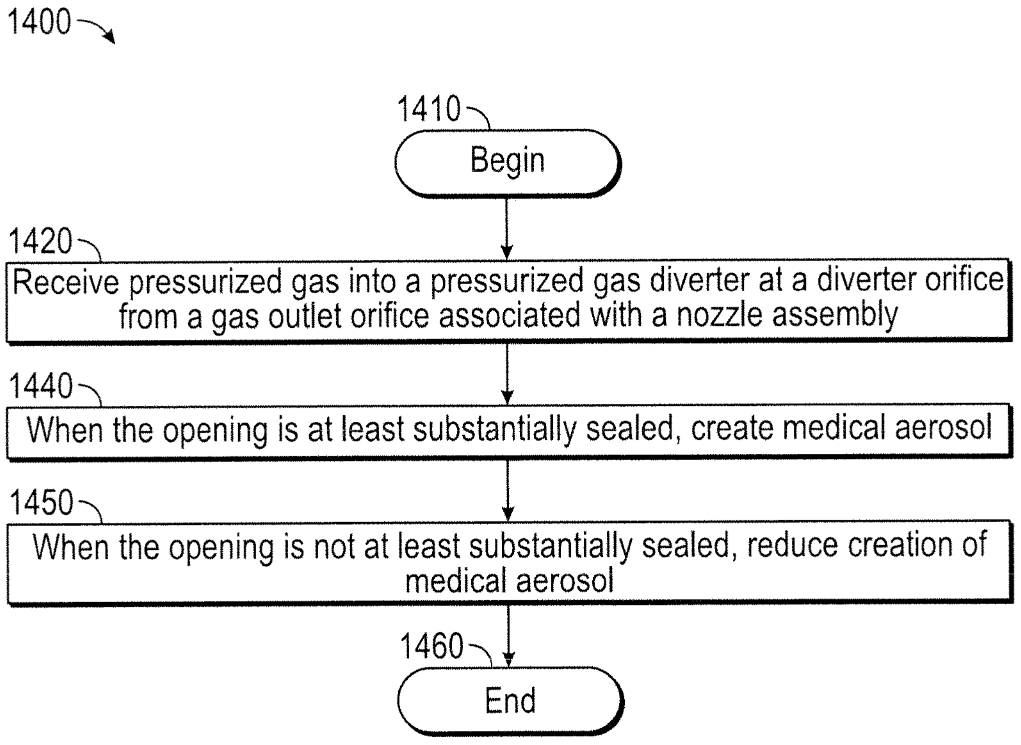
FIG. 14 is a flowchart for a method of deactuating and actuating a nebulizer in response to a living being's breath, according to one embodiment The drawings referred to in this description should not be understood as being drawn to scale unless specifically noted.

FIG. 14 is a flowchart 1400 for a method of deactuating and actuating a nebulizer in response to a living being's breathing through the nebulizer, according to one embodiment.

At 1410, the method begins.

At 1420, referring to FIGS. 7 and 8, pressurized gas is received into a pressurized gas diverter 730 at a diverter orifice 810*b* from a gas outlet orifice 820 associated with a nozzle assembly 750.

At 1440, when the opening 730*a* is at least substantially sealed, medical aerosol is created. For example, medical aerosol is created by permitting pressurized gas that entered the internal medication chamber 710 by shearing across the surface of one or more liquid outlet orifices 610 (FIG. 6B) to mix with medication located in the internal medication chamber 710.

More specifically, refer to FIG. 11, during the initial inhalation, the living being can overcome the flow being introduced into the nebulizer 100 through the gas outlet orifice 820. For example, if an amount of gas, such as 8 LPM of gas, is being introduced into the nebulizer 100 through the pressurized gas fitting 310, the living being could inhale more than that same amount of gas, which in this example is 8 LPM, to start producing a negative gauge pressure in the internal medication chamber 710. Once the living being's breathing has produced a negative gauge pressure in the internal medication chamber 710, the diverter-actuator-deactuator 720 can move down and seal the diverter opening 730*a* creating a "diverter seal 1010." The diverter seal 1010 prohibits gas from exiting the diverter opening 730*a* and prevents additional gas from entering the diverter orifice 810*b* from the nozzle assembly 750's gas outlet orifice 820. Therefore, gas is forced to travel in proximity of the liquid outlet orifices 610 (FIG. 6B) enabling pressurized gas to enter the internal medication chamber 710 and mix with the medication resulting in medical aerosol. The medical aerosol can then travel from the internal medication chamber 710 to the living being through the outlet 210.

At 1450, referring to FIGS. 7 and 8, when the opening 730*a* is not at least substantially sealed, medical aerosol is not created or is reduced. For example, the creation of medical aerosol is reduced or prevented by allowing the pressurized gas that entered the diverter 730 to escape through the opening 730*a* at the top 730*b* of the diverter 730. This may be due to the fact that the living being has not started breathing through nebulizer 100 or because the living being has stopped breathing through nebulizer 100 or because the living being has exhaled through nebulizer 100 or because the living being has reduced their volume of inhalation through nebulizer 100. In the event that the living being stopped breathing through the nebulizer 100, once the living being's inhalation rate is not greater than the flow exiting the gas outlet orifice 820, which in this example is 8 LPM, the opening 730*a* at the top of the diverter 730 is unsealed and the creation of medical aerosol stops or reduced. The term "reduced" is defined as reduced in comparison to when the diverter opening 730*a* is sealed in response to the breathing of the living being. According to one embodiment, an insignificant amount of medical aerosol may be created when the opening 730*a* at the top of the diverter 730 is unsealed.

More specifically, referring to FIG. 9, the diverter 730 is deactuated during periods of non-inhalation due to the opening 730*a* at the top 730*b* of the diverter 730 not being sealed, according to one embodiment. For example, pressurized gas can enter the nozzle assembly 750 through the pressurized gas fitting 310. The pressurized gas can travel up the inner chamber of the nozzle assembly 750 and out the gas outlet orifice 820 located at the top of the nozzle assembly 750. A significant amount of the gas can then move into the pressurized gas diverter 730 through the diverter orifice 810*b* and out the opening 730*a* located at the top 730*b* of the diverter 730. A first portion of the gas that entered the diverter 730 can be vented out of the nebulizer 100 through various openings in the nebulizer 100 without exiting the chamber air outlet 210. A second portion of the gas that entered the diverter 730 may travel to the internal medication chamber 710, however, according to various embodiments, the second portion of gas does not come into close enough proximity of the liquid outlet orifices 610 (FIG. 6B) to produce medical aerosol.

At 1460, the method ends.

As discussed herein, a living being's peak inhalation flow may exceed the flow being delivered into the nebulizer through the gas outlet orifice 820 (FIG. 8). Therefore, according to one embodiment, an additional air inlet valve 1210 (FIG. 12) can be used to enable ambient air to enter the nebulizer to make up the difference between the living being's peak inhalation flow and the flow being delivered through the gas outlet orifice 820 (FIG. 8).

Thus, referring to FIGS. 7 and 8, a breath actuated nebulizer 100 is provided that includes an internal medication chamber 710 and a pressurized gas diverter 730, according to one embodiment. The internal medication chamber 710 is configured for holding a medication that is capable of being converted into a medical aerosol. The pressurized gas diverter 730 includes a diverter orifice 810*b*. The pressurized gas diverter 730 prevents or reduces creation of the medical aerosol when deactuated in response to a lack of breathing and enables creation of the medical aerosol when actuated in response to breathing.

According to another embodiment, the breath actuated nebulizer 100 (FIGS. 1 and 7) includes a housing 120 (FIG. 1), a chamber air outlet 210 (FIG. 7), one or more liquid outlet orifices 610 (FIG. 6B), a gas outlet orifice 820 (FIG. 8) and a pressurized gas diverter 730. The housing 120 (FIG. 1) has an internal medication chamber 710 (FIG. 7) configured for holding a medication that is capable of being converted into a medical aerosol. The chamber air outlet 210 (FIG. 7) is coupled with the internal medication chamber 710 (FIG. 7) for transferring the medical aerosol to a living being. The one or more liquid outlet orifices 610 (FIG. 6B) are configured for permitting pressurized gas to mix with the medication. The gas outlet orifice 820 (FIG. 8) is configured for permitting pressurized gas to shear across the surface of the one or more liquid outlet orifices 610 (FIG. 6B). The gas outlet orifice 820 (FIG. 8) is adjacent to the one or more liquid outlet orifices 610 (FIG. 6B), according to one embodiment. The pressurized gas diverter 730 (FIG. 7) contains a diverter orifice 810*b* (FIG. 8) configured for preventing the pressurized gas from shearing across the surface of the one or more liquid outlet orifices 610 (FIG. 6B) when an opening 730*a* (FIG. 7) in the pressurized gas diverter 730 (FIG. 7) is not at least substantially sealed.

Examples of the subject matter are thus described. Although the subject matter has been described in a language specific to structural features and/or methodological acts, it is to be understood that the subject matter defined in the appended claims is not necessarily limited to the specific features or acts described above. Rather, the specific features and acts described above are disclosed as example forms of implementing the claims.

Various embodiments have been described in various combinations. However, any two or more embodiments may be combined. Further, any embodiment may be used separately from any other embodiment. Features, structures, or characteristics of any embodiment may be combined in any suitable manner with one or more other features, structures, or characteristics.

What is claimed is:

1. A nebulizer comprising:

an internal medication chamber configured for holding a medication;

a pressurized gas diverter comprising a top, a bottom, a wall encompassing an inner chamber, a diverter orifice located at the bottom of the pressurized gas diverter, a diverter opening opposite the diverter orifice and located at the top of the pressurized gas diverter; and a diverter-actuator-deactuator that actuates the pressurized gas diverter by substantially sealing the diverter opening, and deactuates the pressurized gas diverter by unsealing the diverter opening, wherein the opening is configured to divert a pressurized gas from shearing across a surface of a liquid outlet orifice when the diverter opening is at least partially unsealed.

2. The nebulizer of claim 1, further comprising a diverter override mechanism configured to permit creation of medical aerosol when engaged.

3. The nebulizer of claim 1, further comprising a visual indicator that mechanically moves in response to pressure fluctuations within the internal medication chamber.

4. The nebulizer of claim 1, further comprising a gas outlet orifice in proximity of the diverter orifice, wherein a gas flow from the gas outlet orifice is substantially received through the diverter orifice when the pressurized gas diverter is deactuated and wherein the gas flow received through the diverter orifice is substantially less when the pressurized gas diverter is actuated.

5. The nebulizer of claim 1, wherein the diverter-actuator-deactuator actuates the pressurized gas diverter in response to inhalation and deactuates the pressurized gas diverter in response to lack of inhalation.

6. The nebulizer of claim 1, wherein the diverter-actuator-deactuator comprises a flexible material in a bowl shape.

7. The nebulizer of claim 1, wherein the diverter-actuator-deactuator stretches to substantially seal said diverter opening.

8. The nebulizer of claim 5, wherein the diverter-actuator-deactuator has an original shape in response to the lack of inhalation.

9. The nebulizer of claim 5, wherein the diverter-actuator-deactuator has a piston construction that substantially seals the diverter opening in response to the inhalation and unseals the diverter opening in response to the lack of inhalation.

10. The nebulizer of claim 1, wherein the pressurized gas diverter enables creation of a medical aerosol from the medication when actuated in response to inhalation.

11. The nebulizer of claim 10, wherein the pressurized gas diverter reduces production of the medical aerosol when deactuated in response to a lack of breathing, exhalation, or reduced inhalation.

12. The nebulizer of claim 11, wherein the pressurized gas diverter prevents production of the medical aerosol when responsively deactuated.

13. A nebulizer, comprising:

a housing having an internal medication chamber;

a chamber air outlet coupled with the internal medication chamber;

a liquid outlet orifice configured to permit a pressurized gas to mix with a medication;

a gas outlet orifice adjacent the liquid outlet orifice and configured to permit the pressurized gas to shear across a surface of the liquid outlet orifice; and a pressurized gas diverter comprising a top, a bottom, a wall encompassing an inner chamber, a diverter orifice located at the bottom of the pressurized gas diverter, a diverter opening opposite the diverter orifice and located at the top of the pressurized gas diverter;

a diverter-actuator-deactuator that actuates the pressurized gas diverter by substantially sealing the diverter opening, and deactuates the pressurized gas diverter by unsealing the diverter opening, wherein the opening is configured to divert the pressurized gas from shearing across the surface of the liquid outlet orifice when the diverter opening is at least partially unsealed;

wherein a gap between the gas outlet orifice and the diverter orifice remains substantially same when the pressurized gas shears across the surface of the liquid outlet orifice.

14. The nebulizer of claim 13, wherein an amount of flow through the diverter orifice responds to fluctuations of pressure within the internal medication chamber.

15. The nebulizer of claim 13, wherein an amount of flow through the diverter orifice responds to an operator intervention.

16. The nebulizer of claim 13, wherein pressure fluctuations within the internal medication chamber are visually indicated through mechanical movement of a visual indicator.

17. The nebulizer of claim 13, wherein pressure within the internal medication chamber fluctuates in response to a living being's breathing through an outlet of the nebulizer.

18. A nebulizer, comprising:

a housing having an internal medication chamber;

a chamber air outlet coupled with the internal medication chamber;

a liquid outlet orifice configured to permit a pressurized gas to mix with a medication;

a gas outlet orifice adjacent the liquid outlet orifice and configured to permit the pressurized gas to shear across a surface of the liquid outlet orifice;

a pressurized gas diverter comprising a top, a bottom, a wall encompassing an inner chamber, a diverter orifice located at the bottom of the pressurized gas diverter, a diverter opening opposite the diverter orifice and located at the top of the pressurized gas diverter;

a diverter-actuator-deactuator that actuates the pressurized gas diverter by substantially sealing the diverter opening, and deactuates the pressurized gas diverter by unsealing the diverter opening, wherein the opening is configured to divert the pressurized gas from shearing across the surface of the liquid outlet orifice when the diverter opening is at least partially unsealed; and a pressurized gas diverter override mechanism configured to permit creation of medical aerosol when engaged;

wherein a gap between the gas outlet orifice and the diverter orifice remains substantially same when the pressurized gas shears across the surface of the liquid outlet orifice.

19. The nebulizer of claim 18, further comprising a wherein the diverter-actuator-deactuator is configured to actuate the pressurized gas diverter in response to inhalation and deactuate the pressurized gas diverter in response to lack of inhalation.

20. The nebulizer of claim 18, wherein the diverter-actuator-deactuator comprises a flexible material in a bowl shape.

* * * * *